United States Patent [19]
Flashinski et al.

[11] Patent Number: 6,154,607
[45] Date of Patent: Nov. 28, 2000

[54] DEVICE FOR DISPENSING VOLATILE MATERIALS

[75] Inventors: Stanley J. Flashinski, County of Racine; Nancy J. Vnuk, County of Milwaukee; Murthy S. Munagavalasa; Stacey L. Forkner, both of County of Racine; Daniel L. Hurrle, County of Waukesha; Michael E. Short, Racine; Stephen B. Leonard, Caledonia, all of Wis.

[73] Assignee: S. C. Johnson & Son, Inc., Racine, Wis.

[21] Appl. No.: 09/345,918

[22] Filed: Jul. 1, 1999

Related U.S. Application Data

[63] Continuation-in-part of application No. 09/251,170, Feb. 17, 1999.

[51] Int. Cl.[7] .................................................. A61M 16/00
[52] U.S. Cl. ............................................. 392/390; 239/34
[58] Field of Search ...................... 392/386, 390, 392/391, 392, 393, 394, 395; 239/34, 35, 36, 37, 53, 54, 55, 56, 57

[56] References Cited

U.S. PATENT DOCUMENTS

| | | |
|---|---|---|
| 2,742,342 | 4/1956 | Dew et al. . |
| 3,558,055 | 1/1971 | Storchheim . |
| 4,145,001 | 3/1979 | Weyenberg et al. . |
| 4,214,146 | 7/1980 | Schimanski . |
| 4,439,415 | 3/1984 | Hennart et al. . |
| 4,544,592 | 10/1985 | Spector . |
| 5,645,845 | 7/1997 | Neumann et al. . |

FOREIGN PATENT DOCUMENTS

| | | |
|---|---|---|
| 0321729 | 6/1989 | European Pat. Off. . |
| 4239025 | 5/1994 | Germany . |
| 2302507 | 1/1997 | United Kingdom . |

*Primary Examiner*—Sang Paik

[57] ABSTRACT

Disclosed herein are devices for dispensing volatile vapors such as insecticides. Table-like carrier members provide a compartment for the volatile material. One or more table leg structures extend down from a table top to support a cavity in the table top a distance above a burner element. This results in more moderate and uniform heating, thereby permitting efficient release of the volatile material over a longer period of time. In some versions the table leg structures and table top are formed as separate pieces and designed to permit side-to-side ventilation under the volatile.

21 Claims, 6 Drawing Sheets

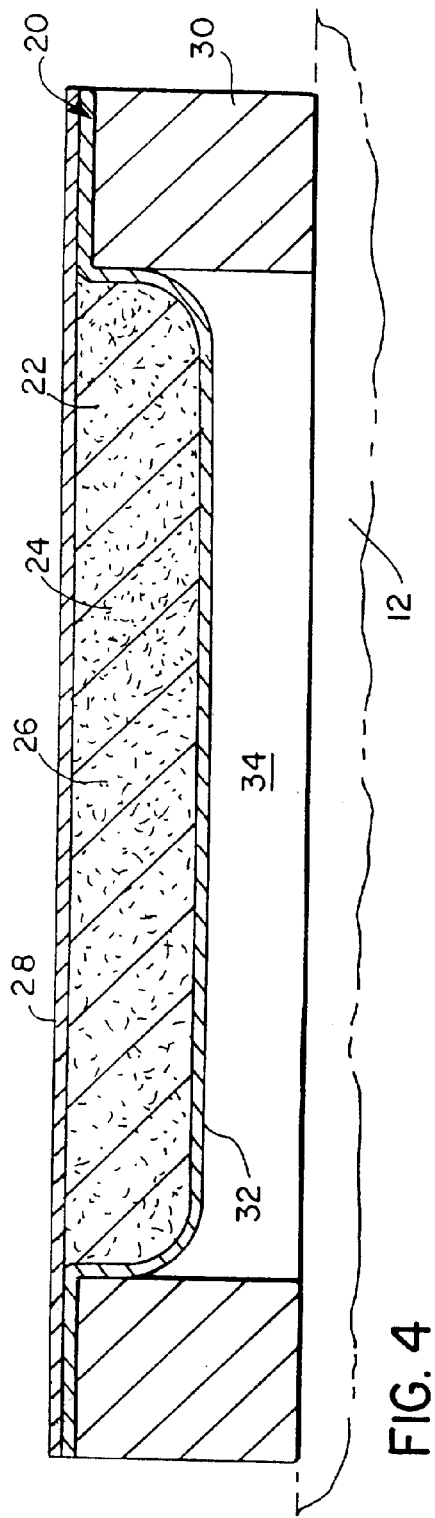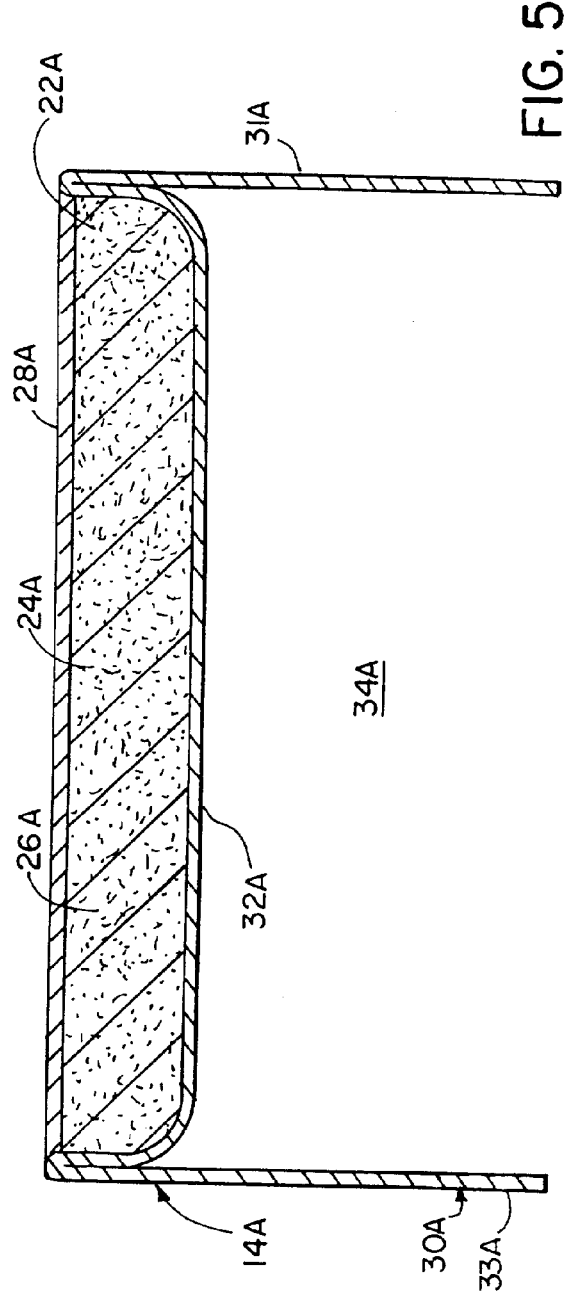

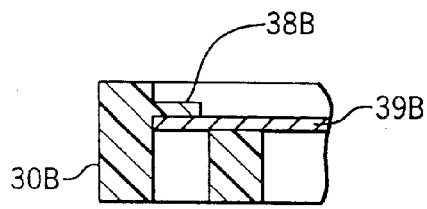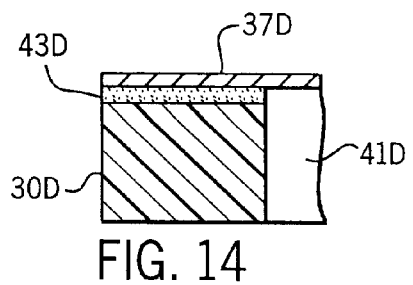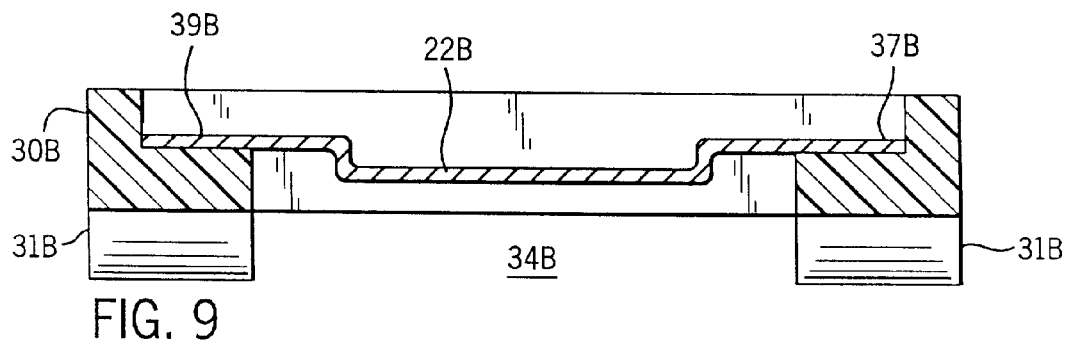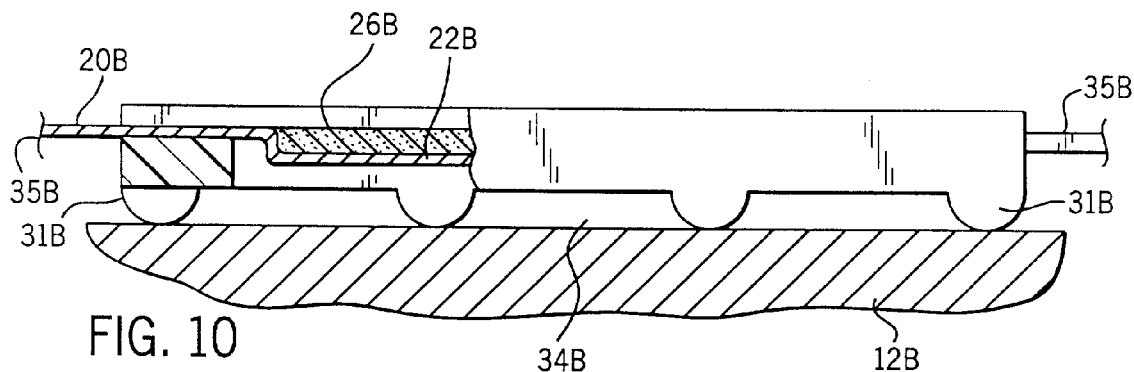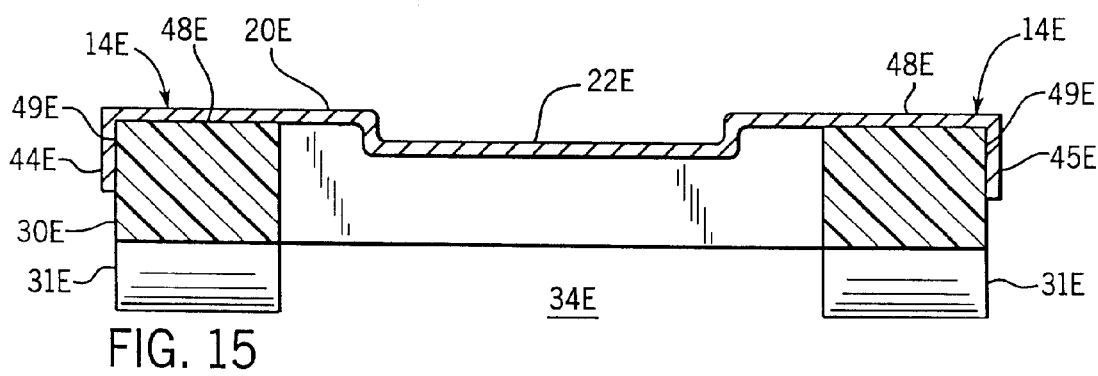

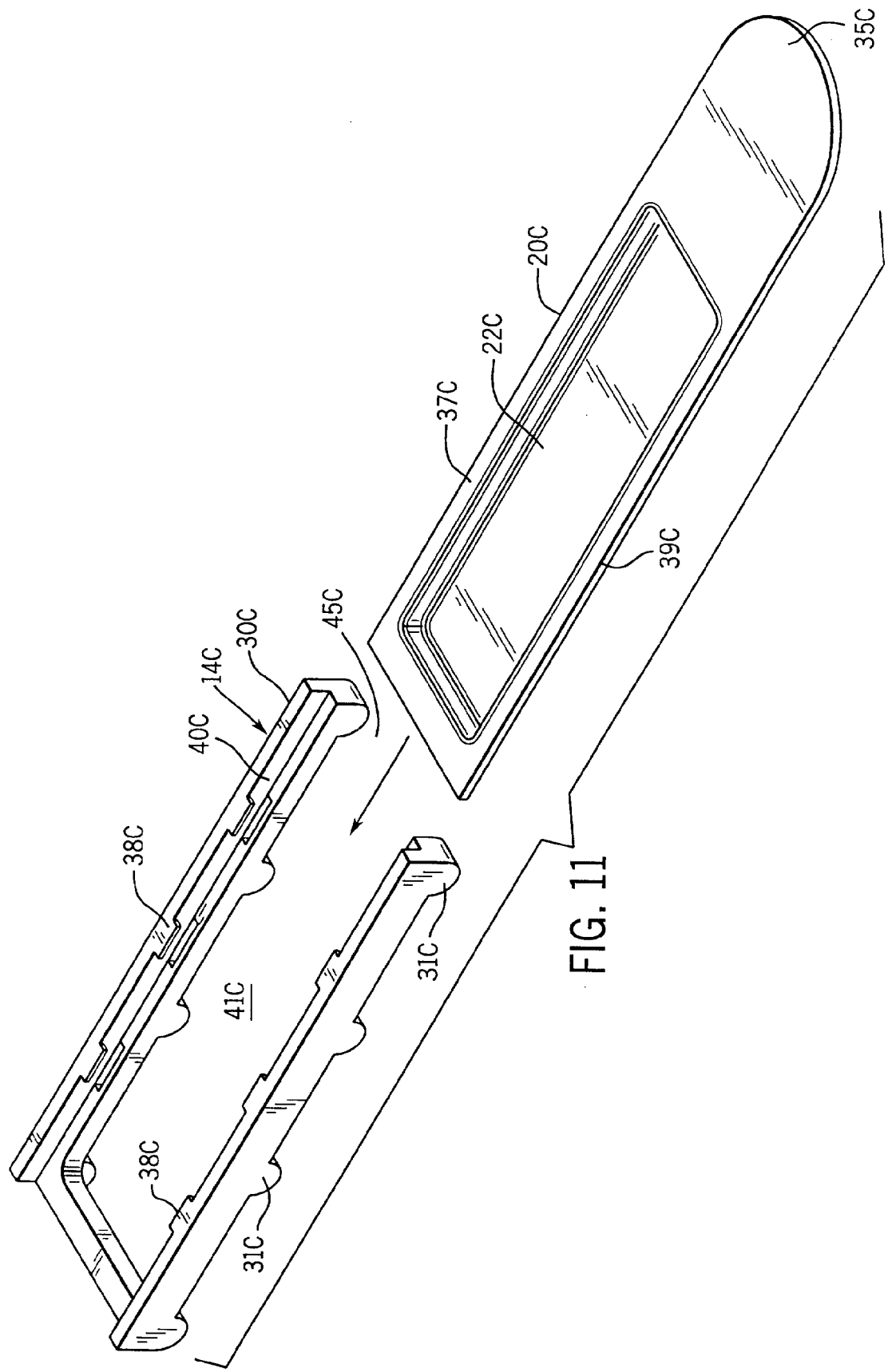

the table top over the support.
DEVICE FOR DISPENSING VOLATILE MATERIALS

CROSS REFERENCES TO RELATED APPLICATIONS

This is a continuation-in-part of application Ser. No. 09/251,170 filed Feb. 17, 1999.

STATEMENT REGARDING FEDERALLY SPONSORED RESEARCH

Not applicable.

BACKGROUND OF THE INVENTION

This invention relates to dispensing volatile materials such as insecticides, insect repellents, and fragrances. More particularly, it relates to devices containing a volatile material which are employed in conjunction with an electrical or other heating apparatus.

It is known in the art to impregnate a solid porous mat with a volatile material, or to place a volatile material in a pan-like metal structure. These mats and pans were placed on heaters to cause the volatile material to vaporize into the atmosphere. One type of heater used for this purpose was sold by S. C. Johnson & Son, Inc. under the trademark FUYI VAPE. See also U.S. Pat. No. 4,439,415 for a general discussion of heater units used for this purpose. The disclosure of this patent, and of all other publications referred to herein, are incorporated by reference as if fully set forth.

A problem with such metal pans is that for typical heaters they could cause the volatile material to be exposed to too much heat. This could cause the volatile to be used up too fast or to degenerate (particularly during extended usage).

The mats had similar problems, and also had significant problems with respect to the mats being exposed to different temperatures across the mat surface. In this regard, low-cost existing heaters often have hotter regions at certain points along their burner surface. The mats therefore had somewhat inefficient vaporization.

The above problems are of increased concern for products designed for use for a week or more. Merely adding additional volatile does not adequately address the problem as prolonged exposure of volatiles to too high temperatures wastes and/or destroys the volatile.

Another design consideration is that existing heaters, for safety and other reasons, often only accept mats or other inserts having a small cross-sectional shape so that they can fit into a small heater opening. Thus, any solution to the above problem needs to take into account size restrictions.

As such, it can be seen that a need exists for an improved volatile dispensing device.

BRIEF SUMMARY OF THE INVENTION

In one aspect, the invention provides a table which is suitable to dispense volatile vapors when heated. The table has a table top with a cavity in its upper surface. A volatile material is placed in the cavity. A support extends downwardly from the table top, the support being constructed and arranged so as to be suitable to be placed on a surface of a heater while leaving an air gap between a bottom of the cavity and a heating surface of the heater. The support extends at least partially radially outward of the cavity (below and/or adjacent the sides of the cavity).

In one preferred form the volatile material is selected from the group consisting of insecticides, insect repellents, fragrances, and deodorizers. A solid substrate (such as cellulose) may be positioned in the cavity, with the substrate being impregnated with the volatile material. Alternatively, other solids, gels, and suitably contained liquids can be used as holders or sources of the volatile material. Also, a permeable membrane extends over the cavity, the table top is made of a thermally conductive material such as a metal, suitable plastic, ceramic, or the like, and the support is made of thermally insulated material such as a heat-resistant plastic, cellulosic material, or ceramic.

In another aspect, the invention provides a device for dispensing volatile vapors. There is a heater having a heating surface. A table of the above kind is positioned adjacent the heating surface. Preferably, the heater is either an electrical resistance heater or a positive temperature co-efficient heater, also referred to as a "PTC heater."

In another preferred form, the table top and support are formed as two separate units. They are connected together by tabs on the support, by adhesive binding between the support and the table top, and/or by bending side portions of The present invention provides a way of holding the volatile up off the burner unit so that there is a temperature step-down before the bottom of the cavity is exposed to heat. Further, the air gap and preferred metal structure serve to spread the heat more uniformly across the cavity. This leads to more efficient use of expensive volatiles as well as reduces degradation due to exposure to excessive temperature over prolonged periods. As a result, inserts can be designed for use for a week, a month, or even several months.

These and still other features of the present invention (e.g. combining such tables with such heaters) will be apparent from the description which follows. The following description is of the preferred embodiments. The claims should be looked to in order to understand the full scope of the invention.

BRIEF DESCRIPTION OF THE DRAWINGS

FIG. 4 is a sectional view taken along line 4—4 of FIG. 2;

FIG. 5 is a sectional view of a first alternative embodiment of a table of the present invention;

FIG. 8 is a sectional view taken along line 8—8 of FIG. 6;

FIG. 9 is a sectional view taken along zig-zag line 9—9 of FIG. 6;

FIG. 10 is a side view of the FIG. 6 embodiment, albeit with a portion broken away, and with the table being positioned on a heating plate;

FIG. 11 is a perspective view of a third embodiment, albeit with the parts being shown prior to assembly and without a volatile in the table top;

FIG. 14 is a sectional view taken along line 14—14 of FIG. 13; and

FIG. 15 is a sectional view of another embodiment, showing the table crimped over the support.

DETAILED DESCRIPTION

Figure 1:
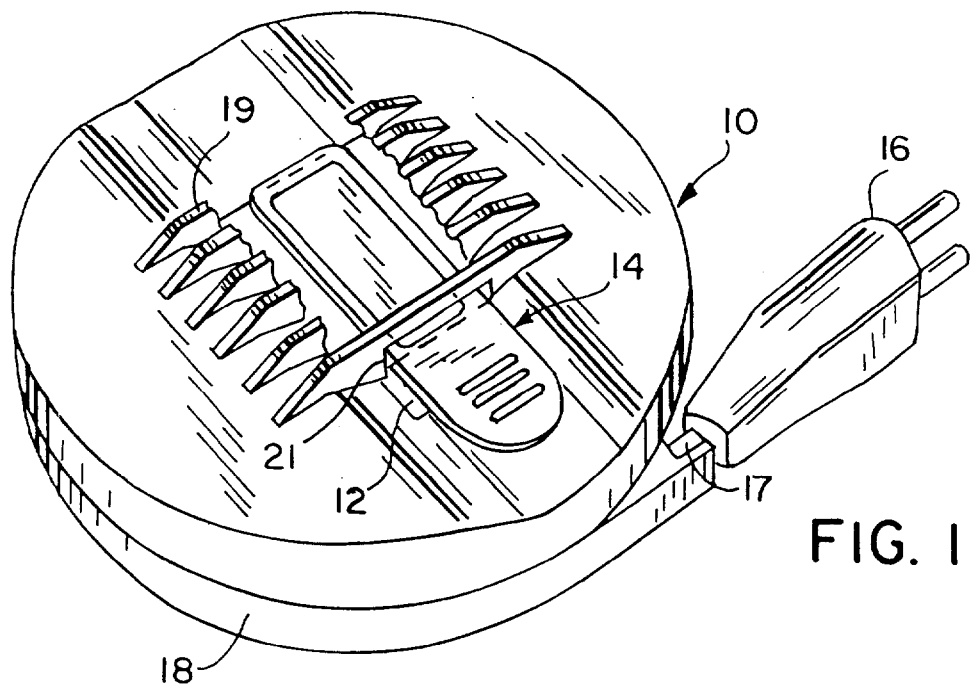
FIG. 1 is a top, partially-fragmented, perspective view showing a device for dispensing volatile materials of the present invention.

In FIG. 1 there is shown an electrical heater, generally 10. The heater is the FUYI VAPE heater previously described, except that the mat previously used with that heater has been replaced with a table of the present invention. The heater is an electrical-resistance heater, and has a flat, upwardly exposed plate 12 adjacent to which is placed a table 14 of the present invention.

An electrical plug 16 (preferably of the self-retracting type) supplies electricity to the heating plate 12 by means of electrical cord 17. During non-use it is almost entirely contained in lower housing 18. As shown at 21, six safety grids are provided (five of which are broken away in FIG. 1 for purposes of illustration).

Although the FUYI VAPE heater is described as a suitable heater, the device of the invention is adapted for use with a wide variety of other electrical and non-electrical heaters available for heating conventional mosquito mats. For example, a conventional, positive temperature co-efficient heater may be substituted for the resistance heater and is preferred in many applications, and other sources of heat, such as flame or catalytically combusted fuel also may be substituted and are widely known to the art.

Figure 2:
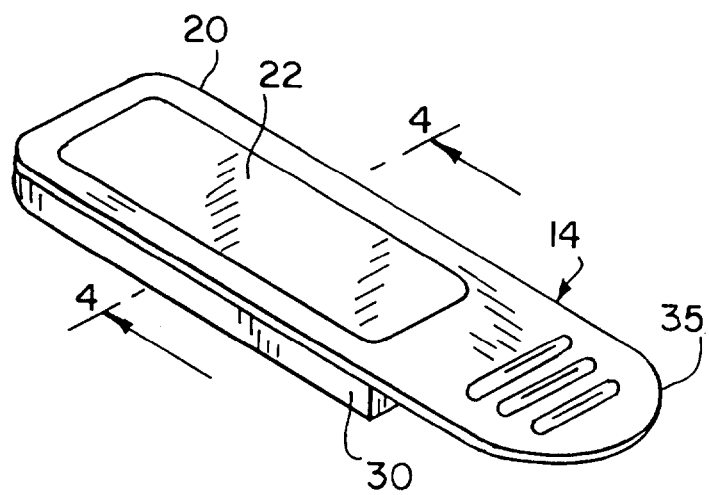
FIG. 2 is a top perspective view of the table of FIG. 1.
Figure 3:
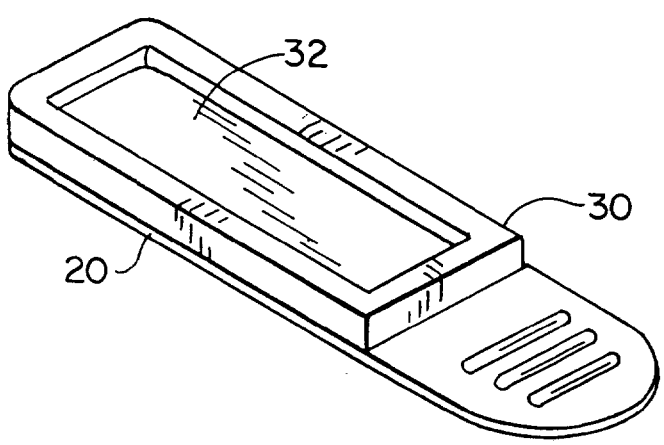
FIG. 3 is a bottom perspective view of the table of FIG. 1.
Figure 6:
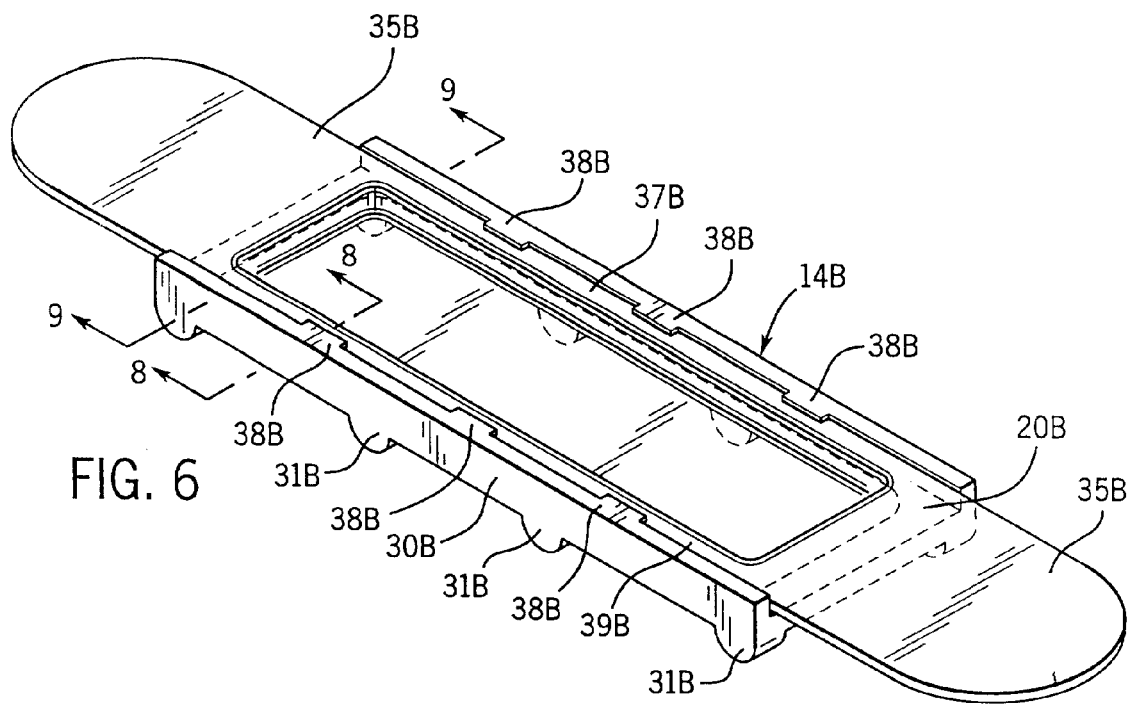
FIG. 6 is a perspective view of an alternative embodiment.
Figure 7:
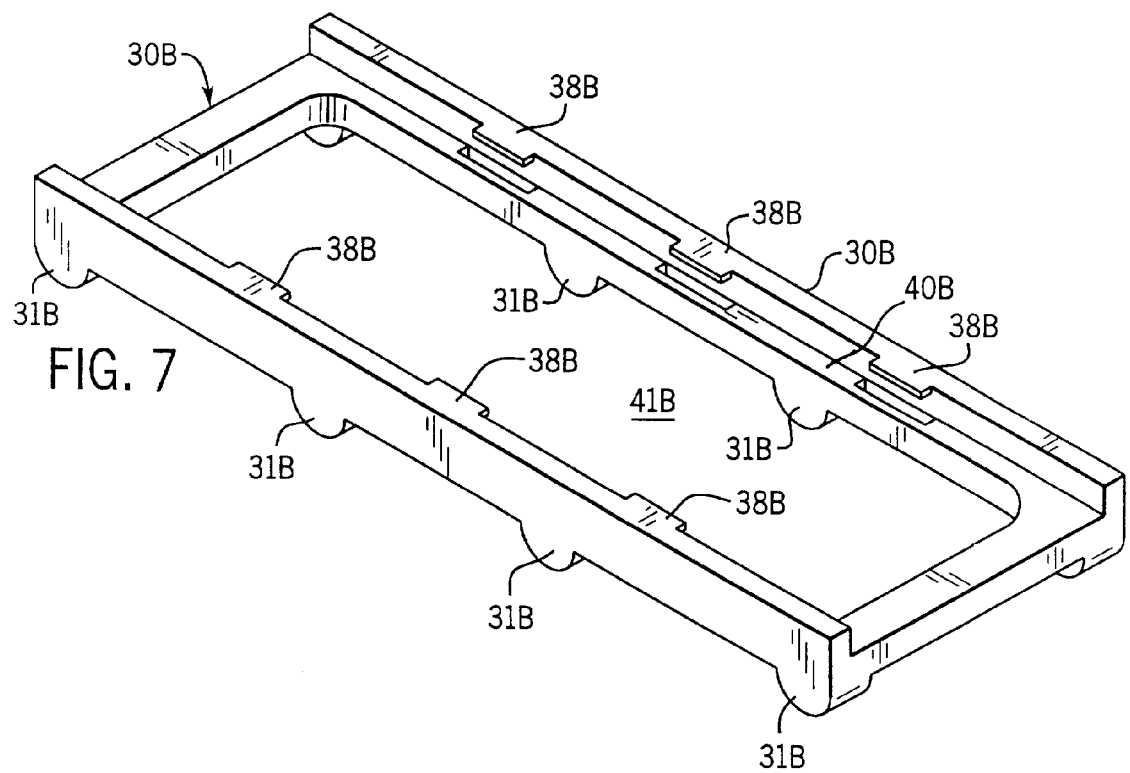
FIG. 7 is a perspective view of the support portion of the FIG. 6 embodiment.

Referring now to FIGS. 2–4, table 14 has a table top 20 made of aluminum (or other metal) having an upwardly-facing cavity 22. Alternatively, the table top 20 can be made of heat-resistant plastic, ceramics, or any otherwise suitable heat resistant material that can transfer heat from the heater to the remaining parts of the table 14. A solid substrate 24 is made of a porous material such as paper or other cellulose-based material. Other solid porous substrates could also be used, such as sintered glass, ceramic, plastic beads, natural or synthetic fabrics, and other absorbent and adsorbent materials. The substrate/mat 24 is impregnated with a volatile 26 and then placed in the cavity 22. The volatile is released from the substrate 24 when the table is heated. Gels and suitably contained liquids can be used in the cavity 22 instead of the solid substrate 24.

Extending over the open portion of cavity 22 and substrate 24 is a permeable membrane 28 that is preferably a laminated membrane having an lower layer which is polyethylene terephthalate and an upper layer which is polyethylene. Membrane 28 further slows release of the volatile 26 from the substrate 24 when the substrate is heated by the heating plate 12. For long-term storage (e.g. on a retailer's shelf), a non-porous removable cover (not shown) is placed over layer 28. See e.g. U.S. Pat. No. 4,145,001. The membrane 28 can be one that presents so little resistance to the escape of vapors that it serves only to confine and protect the source of volatile, whether in liquid, gel, or solid form. However, and preferably, the membrane 28 is selected to restrict volatile release to a desired extent, slowing volatile release from the table and thereby allowing control over the useful life of the table.

Extending downwardly from table top 20 is a support 30, which in one embodiment surrounds the sides of the lower portion of cavity 22. It should, at minimum, have a portion that extends farther outward than the bottom of the cavity 22. In this regard, by "radially outward" we mean that some portion of the structure is radially outward, regardless of whether at the side or below the cavity. In an especially preferred form, none of the support is immediately below the cavity.

The support can be made of an insulative material such as a temperature-resistant cellulosic material or foam or other heat resistant and flame retardant plastic. It can be secured to the table top by a friction fit around the sides of the cavity, by an adhesive such as epoxy, urethane, or acrylic adhesive, or by other means such as double sided tape.

The support 30 is designed to rest on heating plate 12, preferably straddling the burner surface. It thereby supports the cavity 22 (and thus the volatile) above the heating plate 12 with an air gap 34 therebetween. There preferably is also a handle 35, illustrated in FIG. 1, extending from at least one and, optionally and sometimes preferably, two edge locations of the table top 20 for facilitating the insertion and removal of the table 14 on burner plate 12 under safety grids 19. Handle 35 also provides a useful heat sink and radiator for drawing the heat out from cavity 22 and exhausting it to the surrounding air. This effect aids in the even heating of table 20 and especially in controlling and reducing the temperature of the table.

Alternative embodiments are shown in FIGS. 5–15 where similar numerals designate similar components, except with the numerals having an "A", "B", "C", "D" or "E" suffix. Referring to the embodiment 14A shown in FIG. 5, the difference between embodiments 14 and 14A is in the use of a different support. Support 30A is composed of the same material as top 20A (preferably both aluminum). It is formed as one piece during a stamping operation, albeit it has two opposing table legs 31A and 33A which can be bent to positions shown in FIG. 5 (to provide support of the cavity 22A above a heating plate).

As seen in FIGS. 6–10, embodiment 14B is formed in two separate components with support 30B being connected to table top 20B by means of the tabs 38B. These are spaced from the upwardly facing surface 40B so that side portions 37B and 39B of the table top 20B can be slightly flexed and inserted therebetween as seen in FIG. 8. This is facilitated by the table top 20B being composed of a thin flexible material such as aluminum.

Support 30B has a plurality of foot members 31B which position the support 30B above a heating plate 12B with an air gap 34B. Cavity 22B (with volatile 26B) are positioned in opening 41B of support 30B at this point. This affords air circulation from the outside to the air gap 34B and accordingly a cooler operation (see especially FIG. 10). Support 30B can be injection molded from a crystalline heat-resistant PET resinous plastic or any suitable heat-resistant plastic, among the many available.

Referring next to FIG. 11, embodiment 14C is similar to embodiment 14B except that instead of portions 37C and 39C of table top 20C being flexed and inserted under tabs 38C, they are slid between the tabs 38C and the surface 40C of the table top 20C. The spacing of the tabs 38C from the top surface 40C provides a slide track for the table top 20C. An end wall of the support 30C is not present so as to allow passage of cavity 22C into opening 41C. This is indicated at numeral 45C.

Figure 12:
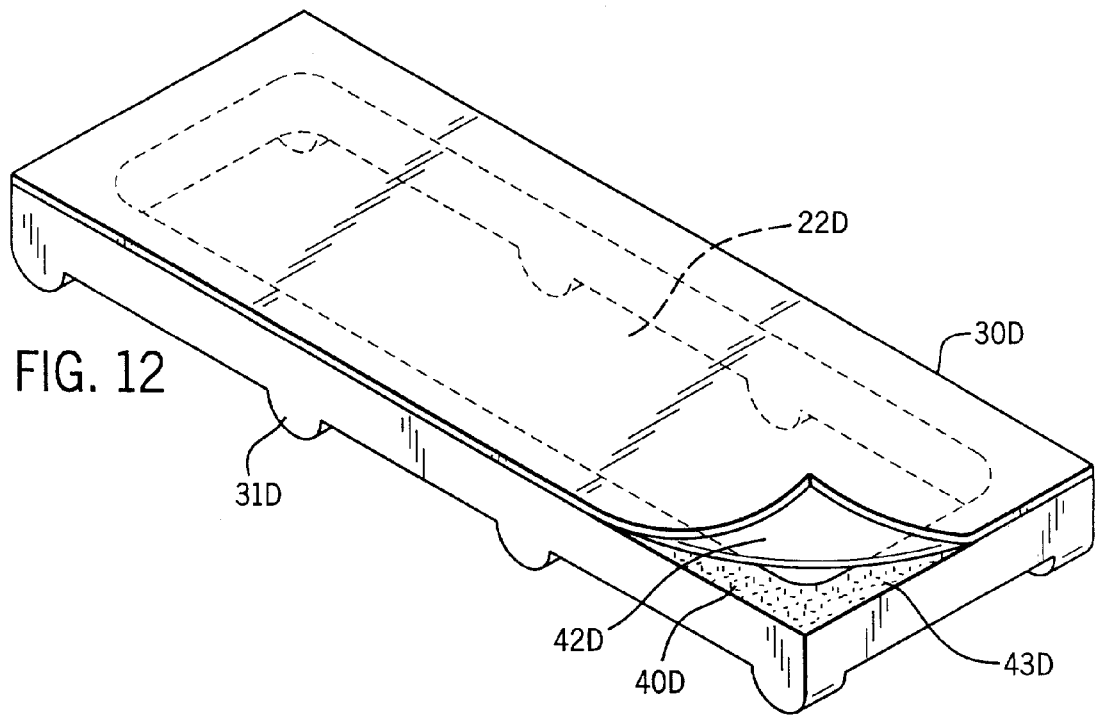
FIG. 12 is a perspective view of another form of support, one which has an upper adhesive section covered by a tear off strip.
Figure 13:
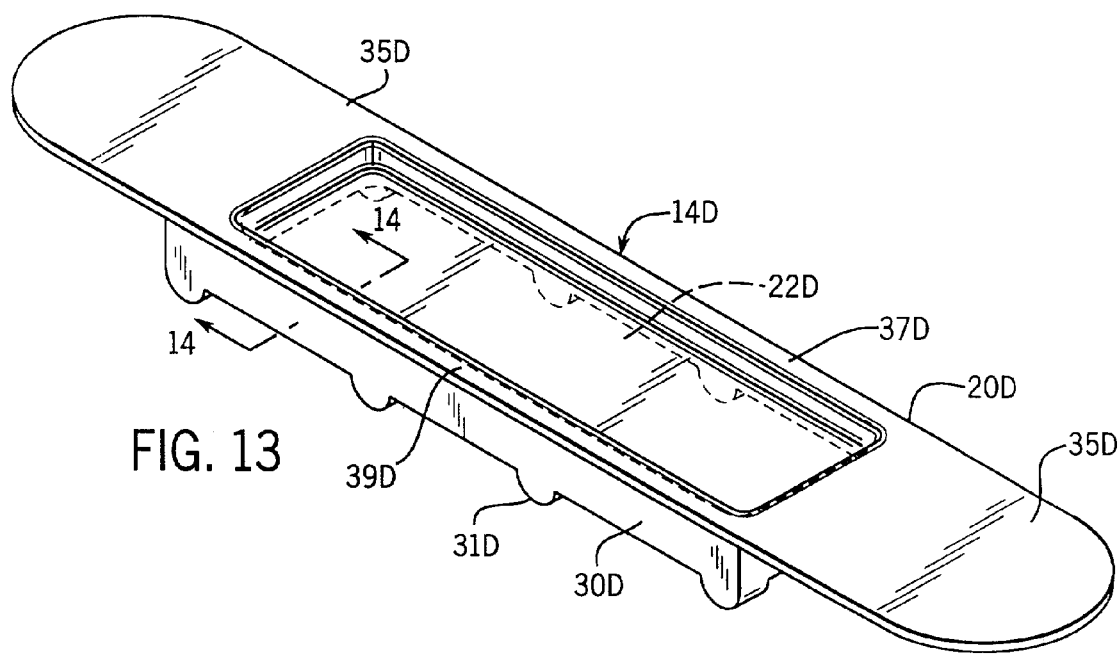
FIG. 13 is a perspective view showing the FIG. 12 support positioned under a table top.

Another support 30D is shown in FIGS. 12–14. It does not employ the fastening or slide tabs 38B/38C shown in embodiments 14B and 14C, respectively. Instead, a peel-away strip 42D is used. An adhesive 43D is placed on the top surface 40D of support 30D for connection to the bottom sections of side portions 37D and 39D of table top 20D. This results in the table 14D shown in FIGS. 13 and 14.

Referring to FIG. 15, tabs like 38B/38C are not employed. Instead the table top 20E has flexible side flanges 44E and 45E. These are bent over and connected by frictional engagement to support 30E by crimping over the tops 48E and side edges 49E of the support member 30E. This provides an air gap 34E between cavity 22E and a heating plate such as 12B.

An important feature of the invention is that at least part of the support (preferably all) is not directly under the cavity, so as to thereby create an air gap. This gap slows heat transfer from the heating plate 12, and thus creates a step-down in temperature from the burner plate temperature and helps to evenly distribute the heat across the floor of cavity 22 (with a resulting slower release of insecticide and less heat-caused degradation of insecticide).

The embodiments shown in FIGS. 6–11 are particularly well suited for use as they not only provide an air gap, they also allow for air to pass sideways between the air gap and the outside. Slower release, assisted by permeable membranes 28 and 28A, results in sustained release of the insecticide over a longer period, thereby permitting inserts to be created which can be effectively used for a week or longer.

While insecticide 26 has been illustrated in conjunction with the impregnation of a solid substrate 24, a liquid or gel could be used without the solid substrate, in conjunction with porous membrane 28. See e.g. U.S. Pat. No. 5,645,845 for gel-based systems. In one form, we used a mixture of transfluthrin with a silica gel such as the gel sold under the trade name Cabosil.

The volatile material is preferably one of (or mixtures of) known insecticides and insect repellents. Particularly preferred are organic phosphorous insecticides, lipidamide insecticides, natural repellents as citronella oil, natural pyrethrins and pyrethrum extract, and synthetic pyrethroids. Suitable synthetic pyrethroids are acrinathrin, allethrin as D-allethrin, Pynamin®, benfluthrin, bifenthrin, bioallethrin as Pynamin Forte®, S-bioallethrin, esbiothrin, esbiol, bioresmethrin, cycloprothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, tau-fluvalinate, kadethrin, permethrin, phenothrin, prallethrin as Etoc®, resmethrin, tefluthrin, tetramethrin or tralomethrin. Other volatile insecticides as described in U.S. Pat. No. 4,439,415 can also be employed. Most preferred is transfluthrin.

Deodorizers may also be used such as a terpene based deodorizer fragrance. Anti-oxidants may also be delivered in this manner.

Further, disinfectants may be used such as glycols, trimethylene, and dipropylene. In addition, organic acids which are compatible with the use of the substrate and the atmosphere can also be utilized.

It should be understood that terms such as top and downwardly/bottom are used herein with respect to the most typical orientation. However, for heater units with vertical or other heating surfaces these terms are intended to mean directions away from and toward the heater, respectively.

The invention is not to be limited to the specific embodiments shown. Rather, the claims should be looked to in order to appreciate the full scope of the claimed invention.

INDUSTRIAL APPLICABILITY

The invention provides a device for dispensing volatile materials such as insecticides. The device is particularly useful in controlling mosquitoes over extended periods.

What is claimed is:

1. A table which is suitable to dispense volatile vapors when heated, the table comprising:

a table top having in its upper surface a cavity;

a volatile material placed in the cavity; and a support extending downwardly from the table top, the support being constructed and arranged so as to be suitable to be placed on a surface of a heater while leaving an air gap between a bottom of the cavity and a heating surface of the heater, the support including a side opening so as to allow air to flow from outside the support into the air gap;

wherein the support extends at least partially radially outward of the cavity.

2. The table of claim 1, wherein the volatile material is selected from the group consisting of insecticides, insect repellents, fragrances, and deodorizers.

3. The table of claim 1, wherein a porous solid substrate is positioned in the cavity and the volatile material impregnates the substrate.

4. The table of claim 3, wherein a gel mixed with the volatile is positioned in the cavity.

5. The table of claim 4, further comprising a permeable membrane extending over the cavity.

6. The table of claim 4, wherein the permeable membrane is selected to restrict volatile release to a desired extent, slowing volatile release from the table.

7. The table of claim 1, wherein the table top is made of a material selected from the group consisting of metal, heat resistant plastic, and ceramics.

8. The table of claim 1, wherein the support is made of a thermally insulating, heat resistant material.

9. The table of claim 8, wherein the thermally insulating, heat resistant material is selected from the group consisting of cellulose, heat resistant plastics, and ceramics.

10. The table of claim 1, wherein the support includes at least two side openings so as to allow air to flow from outside the support into the air gap.

11. The table of claim 1, wherein the table top and the support are formed as two separate units.

12. The table of claim 11, wherein the support includes a plurality of foot members.

13. The table of claim 12, wherein the support includes tab members spaced from an upwardly facing surface of the support to receive a portion of the table top, and the table top is made of a flexible material.

14. The table of claim 13, wherein the support also includes a slide track under a tab and the table top includes a flange portion to be placed therein.

15. The table of claim 12, wherein the support includes an adhesive for attaching the support to the table top.

16. The table of claim 12, wherein the table top includes flexible flange portions for frictional engagement with the support.

17. The table of claim 1, wherein at least one handle extends from the table at an edge location for a distance sufficient to extend beyond the heater surface when the table is placed thereon to exhaust surplus heat from the table to the surrounding air.

18. The table of claim 17, further comprising a permeable membrane extending over the cavity.

19. The table of claim 18, wherein the permeable membrane is selected to restrict volatile release to a desired extent, slowing volatile release from the table.

20. A device for dispensing volatile vapors, comprising:

a heater having a heating surface; and a table of claim 1 positioned adjacent the heating surface.

21. The device of claim 20 wherein the heater is one of a resistance heater and a PTC heater.

* * * * *